United States Patent
Brassart et al.

(10) Patent No.: US 10,499,668 B2
(45) Date of Patent: *Dec. 10, 2019

(54) NUTRITIONAL PRODUCTS COMPRISING HUMAN MILK OLIGOSACCHARIDES AND METHODS FOR MANUFACTURE THEREOF

(75) Inventors: Dominique Brassart, Chavannes-pres-renens (CH); Gyula Dekany, Queensland (AU); Peter Erdmann, Bern (CH); Andrea Schwarz, Bern (CH); Norbert Sprenger, Savigny (CH)

(73) Assignee: Societe des Produits Nestle S.A., Vevey (CH)

( * ) Notice: Subject to any disclaimer, the term of this patent is extended or adjusted under 35 U.S.C. 154(b) by 1586 days.

This patent is subject to a terminal disclaimer.

(21) Appl. No.: 14/117,424

(22) PCT Filed: May 10, 2012

(86) PCT No.: PCT/EP2012/058639
§ 371 (c)(1),
(2), (4) Date: Nov. 13, 2013

(87) PCT Pub. No.: WO2012/156273
PCT Pub. Date: Nov. 22, 2012

(65) Prior Publication Data
US 2014/0248415 A1    Sep. 4, 2014

(30) Foreign Application Priority Data
May 13, 2011    (EP) .................................... 11166109

(51) Int. Cl.
| | | |
|---|---|---|
| A23L 5/00 | (2016.01) | |
| C07H 5/06 | (2006.01) | |
| C07H 7/027 | (2006.01) | |
| C07H 15/18 | (2006.01) | |
| A23L 29/30 | (2016.01) | |
| A23L 33/00 | (2016.01) | |
| A23L 33/125 | (2016.01) | |
| A23L 7/00 | (2016.01) | |

(52) U.S. Cl.
CPC ................. *A23L 5/00* (2016.08); *A23L 29/30* (2016.08); *A23L 33/00* (2016.08); *A23L 33/40* (2016.08); *C07H 5/06* (2013.01); *C07H 7/027* (2013.01); *C07H 15/18* (2013.01); *A23L 7/00* (2016.08); *A23L 33/125* (2016.08); *A23V 2002/00* (2013.01)

(58) Field of Classification Search
CPC ............ A23V 2002/00; A23V 2250/28; A23V 2300/28; A23L 1/296; A23L 1/09; A23L 1/29; A23L 5/00; A23L 29/30; A23L 33/00; A23L 33/40; A23L 33/125; C07H 15/18; C07H 5/06; C07H 7/027
USPC ........................................ 426/588, 658, 801
See application file for complete search history.

(56) References Cited

U.S. PATENT DOCUMENTS 6,146,670 A    11/2000    Prieto et al.

FOREIGN PATENT DOCUMENTS

| WO | 0012747 | 3/2000 |
| WO | 2010115934 | 10/2010 |

OTHER PUBLICATIONS

Rencurosi et al., "Human milk oligosaccharides: an enzymatic protection step simplifies the synthesis of 3'- and 6'-O-sialyllactose and their analogues," Carbohydrate Research 337.6 (2002): 473-483.

*Primary Examiner* — Jyoti Chawla
(74) *Attorney, Agent, or Firm* — K&L Gates LLP

(57) ABSTRACT

A method for the manufacture an infant formula or an infant nutritional product comprising mixture of human milk oligosaccharides is disclosed. The method involves the catalytic hydrogenolysis of compounds of the general formula 1 and 2 with particular oligosaccharide profiles.

24 Claims, 1 Drawing Sheet

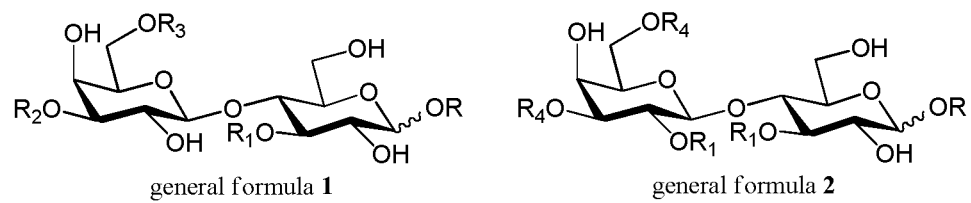
general formula 1    general formula 2

NUTRITIONAL PRODUCTS COMPRISING HUMAN MILK OLIGOSACCHARIDES AND METHODS FOR MANUFACTURE THEREOF

CROSS REFERENCE TO RELATED APPLICATIONS

The present application is a National Stage of International Application No. PCT/EP2012/058639, filed on May 10, 2012, which claims priority to European Patent Application No. 11166109.6, filed May 13, 2011, the entire contents of which are being incorporated herein by reference.

FIELD OF INVENTION

The present invention relates to methods for the manufacture infant nutritional product or infant formula comprising oligosaccharides, in particular oligosaccharides found in human milk. The invention further relates to nutritional compositions comprising such human milk oligosaccharides.

BACKGROUND OF INVENTION

Human milk oligosaccharides (HMOs) are carbohydrates which have gained much interest in recent years. In particular the synthesis of these HMOs has increased significantly due to the role of HMOs in numerous biological processes occurring in humans. HMOs play a vital role in the early development of young children. Furthermore, the importance of HMOs in the maturation of the immune system and their prognostic use as immunomodulators underlines their importance.

A natural source of such HMOs is mammalian milk. Mammalian milk contains up to 10% HMOs. To date the structure of at least 115 HMOs has been determined while the mass spectra (MS) data has suggested a presence of almost 130 HMOs (Newburg and Neubauer, 1995, Carbohydrates in milks: Analysis, quantities and significance. In: Handbook of Milk Composition (R. G. Jensen, ed.), pp. 273-249, Academic Press, San Diego, USA).

The 115 human milk oligosaccharides, the structures of which have been determined to date, can be grouped into 13 categories based on their core structures. Such 13 categories structures are exemplarily shown in table 1 below (see also Urashima et al., Advanced Dairy Chemistry, Volume 3: Lactose, Water, Salts and Minor Constituents, 2009, pp. 295-349; and TADASU URASHIMA et al, MILK OLIGOSACCHARIDES, Nova Biomedical Books, New York, 2011, ISBN: 978-1-61122-831-1).

TABLE 1

13 different core structures of human milk oligosaccharides (HMOs)

| No | Abbreviation | Core structure |
|---|---|---|
| 1 | Lactose | Gal(β1-4)Glc |
| 2 | Lacto-N-tetraose (LNT) | Gal(β1-3)GlcNAc(β1-3)Gal(β1-4)Glc |
| 3 | Lacto-N-neotetraose (LNnT) | Gal(β1-4)GlcNAc(b 1-3)Gal(β1-4)Glc |
| 4 | Lacto-N-hexaose (LNH) | Gal(β1-4)GlcNAc(β1-6)<br>    \|<br>    Gal(β1-4)Glc<br>    \|<br>Gal(β1-3)GlcNAc(β1-3) |
| 5 | Lacto-N-neohexaose (LNnH) | Gal(β1-4)GlcNAc(β1-6)<br>    \|<br>    Gal(β1-4)Glc<br>    \|<br>Gal(β1-4)GlcNAc(β1-3) |
| 6 | para-Lacto-N-hexaose (para-LNH)) | Gal(β1-3)GlcNAc(β1-3)Gal(β1-4)GlcNAc(β1-3)Gal(β1-4)Glc |
| 7 | para-Lacto-N-neohexaose (para-LNnH) | Gal(β1-4)GlcNAc(β1-3)Gal(β1-4)GlcNAc(β1-3)Gal(β1-4)Glc |
| 8 | Lacto-N-octaose (LNO) | Gal(β1-4)GlcNAc(β1-3)Gal(β1-4)GlcNAc(β1-6)<br>    \|<br>    Gal(β1-4)Glc<br>    \|<br>Gal(β1-3)GlcNAc(β1-3) |
| 9 | Lacto-N-neooctaose (LNnO) | Gal(β1-3)GlcNAc(β1-3)Gal(β1-4)GlcNAc(β1-6)<br>    \|<br>    Gal(β1-4)Glc<br>    \|<br>Gal(β1-4)GlcNAc(β1-3) |
| 10 | Iso-Lacto-N-octaose (iso-LNO) | Gal(β1-3)GlcNAc(β1-3)Gal(β1-4)GlcNAc(β1-6)<br>    \|<br>    Gal(β1-4)Glc<br>    \|<br>Gal(β1-3)GlcNAc(β1-3) |
| 11 | para-Lacto-N-octaose (para-LNO) | Gal(β1-3)GlcNAc(β1-3)Gal(β1-4)GlcNAc(β1-3)Gal(β1-4)GlcNAc(β1-3)Gal(β1-4)Glc |
| 12 | Lacto-N-decaose (LND) | Gal(β1-4)GlcNAc(β1-6)<br>    \|<br>    Gal(β1-4)GlcNAc(β1-6)<br>    \|                               \|<br>Gal(β1-3)GlcNAc(β1-3)   Gal(β1-4)Glc<br>                           \|<br>                       Gal(β1-3)GlcNAc(β1-3) |
| 13 | Lacto-N-neodecaose (LNnD) | Gal(β1-4)GlcNAc(β1-6)<br>    \|<br>    Gal(β1-4)GlcNAc(β1-6)<br>    \|                               \|<br>Gal(β1-4)GlcNAc(β1-3)   Gal(β1-4)Glc<br>                           \|<br>                       Gal(β1-3)GlcNAc(β1-3) |

Due to the large number of HMOs and their low concentrations in mammalian milk, an isolation of HMOs from mammalian milk is a difficult task. It is therefore difficult to provide suitable HMOs replacements in foods, particularly in infant formulae which display at least part of the entire spectrum of HMOs.

Although methods for the manufacture of HMOs are known, be it chemically or enzymatically, such manufacturing methods do not allow the preparation of mixtures of HMOs. Preparing such mixtures of HMOs on the basis of individually designed syntheses of single HMOs is furthermore costly and may not resemble the large variety of naturally occurring HMOs.

There is a need to provide a means for the manufacture of a mixture of HMOs wherein the mixture of HMOS has a profile which resembles a mixture of HMOs as found in human milk.

There is also a need to be able to provide a method for the manufacture of HMOs on a relatively large scale, which avoids the use of complicated and expensive methods such as those methods which utilises biotechnology.

There is a need to provide a method, which allows for the manufacture of a mixture of HMOs on a large scale.

SUMMARY OF INVENTION

In an aspect of the invention a method for the manufacture of an infant formula or a infant nutritional product comprising a mixture of human milk oligosaccharides (HMOs) is disclosed. The method comprises subjecting a mixture of at least two compounds selected from the group comprising compounds of general formulae 1 and 2 to catalytic hydrogenolysis to remove the R group.

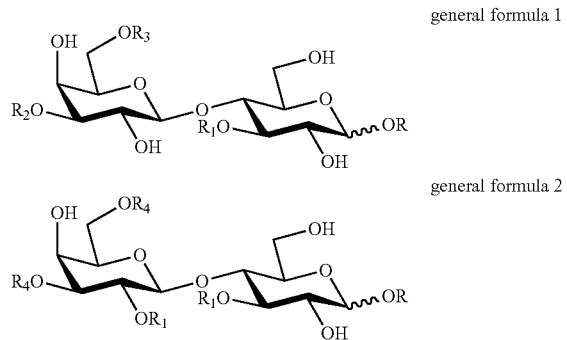

R is a group removable by catalytic hydrogenolysis,
$R_1$ is independently fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_4$ is independently sialyl or H,
and salts thereof,
with the proviso that at least one of $R_1$ or $R_4$ is not H in general formula 2.

A particular profile of oligosaccharides, or a particular ratio of oligosaccharides is selected to best correspond to profile or ratio in human breast milk.

In a further aspect an infant nutritional product or an infant formula is disclosed. The infant nutritional product or the infant formula comprise a mixture of human milk oligosaccharides wherein the mixture is obtainable by the method of the invention.

BRIEF DESCRIPTION OF DRAWINGS

FIG. 1 shows a composition comprising a mixture of at least two compounds selected from the group comprising compounds of general formulae 1 and 2.

DETAILED DESCRIPTION

For a complete understanding of the present invention and the advantages thereof, reference is made to the following detailed description.

It should be appreciated that various embodiments of the present invention can be combined with other embodiments of the invention and are merely illustrative of the specific ways to make and use the invention and do not limit the scope of the invention when taken into consideration with the claims and the following detailed description.

Preferably, the object underlying the present invention is solved by providing a composition comprising a mixture of at least two compounds selected from the group comprising compounds of general formulae 1 and 2 and as shown in FIG. 1.

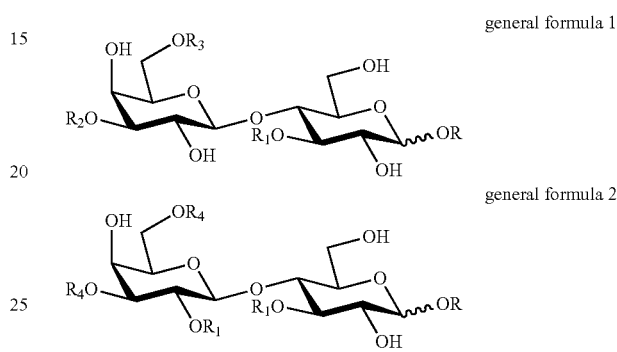

wherein R is a group removable by catalytic hydrogenolysis,
$R_1$ is independently fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_4$ is independently sialyl or H,
and salts thereof,
with the proviso that at least one of $R_1$ or $R_4$ is not H in general formula 2.

A mixture of HMOs is manufactured by catalytic hydrogenolysis of compounds of general formulae 1 and 2.

In the context of the present invention the expression "group removable by catalytic hydrogenolysis" refers to groups, whose C—O bond is cleaved by addition of hydrogen in the presence of a hydrogenolysis catalyst. The hydrogenolysis catalyst is used in the presence of hydrogen gas under pressure and with heat. The hydrogenolysis catalyst can be for example palladium, Raney nickel, palladium on charcoal or palladium black or another appropriate metal catalyst known for use in hydrogenolysis. Thus the use of the hydrogenolysis catalyst in the present invention results in the regeneration of —OH group from the R groups of compounds of general formulae 1 and 2. The R groups of this type are known (see e.g. P. G. M. Wuts and T. W. Greene: *Protective Groups in Organic Synthesis*, John Wiley & Sons (2007)). Suitable R groups include benzyl, diphenylmethyl (benzhydryl), 1-naphthylmethyl, 2-naphthylmethyl or triphenylmethyl (trityl) groups, each of which may be optionally substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen. Preferably, such substitution, if present, is on the aromatic ring(s). Particularly preferred protecting group is benzyl optionally substituted with one or more groups selected from alkyl or halogen. More preferably, the protecting group is selected from unsubstituted benzyl, 4-chlorobenzyl and 4-methylbenzyl. These particularly preferred and more preferable protecting groups have the advantage that the by-products of the hydrogenolysis are exclusively toluene or substituted toluene. Such by-products can easily be removed even in multi ton scales from water soluble oligosaccharide products via evaporation and/or extraction processes.

Additionally, the term "fucosyl" within the context of the present invention preferably means a L-fucopyranosyl group attached to the oligosaccharide of compounds of general formulae 1 and 2 by an α-interglycosidic linkage, such that:

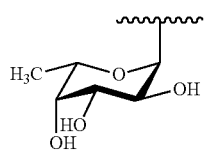

"N-acetyl-lactosaminyl" group within the context of the present invention preferably means the glycosyl residue of N-acetyl-lactosamine (LacNAc, Galpβ1-4GlcNAcp) of compounds of general formulae 1 and 2 links with β-linkage such that:

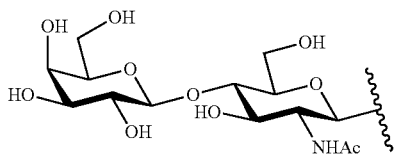

Furthermore, the term "Lacto-N-biosyl" group within the context of the present invention preferably means the glycosyl residue of lacto-N-biose (LNB, Galpβ1-3GlcNAcp) of compounds of general formulae 1 and 2 links with β-linkage such that:

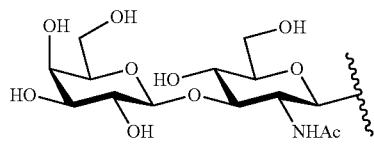

The term "Sialyl" within the context of the present invention preferably means the glycosyl residue of sialic acid (N-acetyl-neuraminic acid, Neu5Ac)) of compounds of general formulae 1 and 2 links with β-linkage such that:

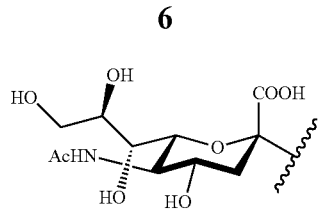

The term "glycosyl residue comprising one or more N-acetyl-lactosaminyl and/or one or more lacto-N-biosyl units" within the context of the present invention preferably means a linear or branched structure comprising the said units that are linked to each other by interglycosidic linkages.

According to the method mentioned above, at least two compounds selected from the group comprising compounds of general formulae 1 and 2 wherein R is a group removable by catalytic hydrogenolysis are provided. Such a mixture of compounds is preferably as noted is at least two, however three, four, five, two to five, five to ten, two to ten, two to twenty, three to twenty, four or even five to twenty, or even more of the compounds selected from the group comprising compounds of general formulae 1 and 2.

The claimed method is based upon the utilisation of at least two compounds selected from the group comprising compounds characterized by general formulae 1 and 2 defined above in catalytic hydrogenolysis. This reaction typically takes place in a protic solvent or in a mixture of protic solvents. A protic solvent may be selected from the group consisting of water, acetic acid or $C_1$-$C_6$ alcohols. A mixture of one or more protic solvents with one or more suitable aprotic organic solvents partially or fully miscible with the protic solvent(s) (such as THF, dioxane, ethyl acetate or acetone) may also be used. Water, one or more $C_1$-$C_6$ alcohols or a mixture of water and one or more $C_1$-$C_6$ alcohols are preferably used as the solvent system. Solutions containing the carbohydrate derivatives in any concentration or suspensions of the carbohydrate derivatives in the solvent (s) used are also applicable. The reaction mixture is stirred at a temperature in the range of 10-100° C., preferably between 20-50° C., in a hydrogen atmosphere of 1-50 bar absolute (100 to 5000 kPa) in the presence of a catalyst such as palladium, Raney nickel or any other appropriate metal catalyst, preferably palladium on charcoal or palladium black, until reaching the completion of the reaction. Transfer hydrogenation may also be performed, when the hydrogen is generated in situ from cyclohexene, cyclohexadiene, formic acid or ammonium formate. Addition of organic or inorganic bases or acids and/or basic and/or acidic ion exchange resins can also be used to improve the kinetics of the hydrogenolysis. The use of basic substances is especially preferred when halogen substituents are present on the substituted benzyl moieties of the precursors and/or the formation of mannosamine base is desirable. Preferred organic bases include, but are not limited to, triethylamine, diisopropyl ethylamine, ammonia, ammonium carbamate and diethylamine. An organic or an inorganic acid is favourably used as a co-solvent or additive in cases when mannosamine salts are the intended products. Preferred acids include, but are not limited to, formic acid, acetic acid, propionic acid, chloroacetic acid, dichloroacetic acid, trifluoroacetic acid, HCl and HBr. The conditions proposed above allow simple, convenient and delicate removal of the solvent(s) giving rise to pure HMO mixture or blend.

In a preferred embodiment at least two compounds selected from the group comprising compounds characterized by general formulae 1 and 2 defined above are subjected to catalytic hydrogenolysis to provide at least two HMOs. The catalytic hydrogenolysis can be performed in water or in aqueous alcohol, preferably in water, water/methanol or water/ethanol mixture (alcohol content: 10-50 v/v %). The catalytic hydrogenolysis is performed at a temperature of between 15-65° C., preferably between 40-60° C. The catalyst concentration may range from 0.4% to 1.2% (weight of the metal content based on the weight of the starting carbohydrate mixture).

The compounds of general formulae 1 are defined under general formulae 1a, 1b. The compounds of general formulae 2 are defined under general formulae 2 below.

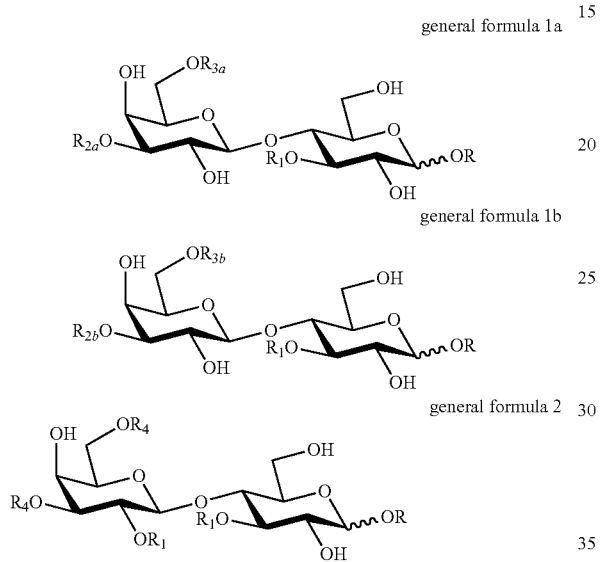

general formula 1a general formula 1b general formula 2 wherein R, $R_1$ and $R_4$ are as defined above,
$R_{2a}$ is N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue,
$R_{3a}$ is H or N-acetyl-lactosaminyl group optionally substituted with a lacto-N-biosyl group; any N-acetyl-lactosaminyl and lacto-N-biosyl group can be substituted with one or more sialyl and/or fucosyl residue,
$R_{2b}$ is lacto-N-biosyl group optionally substituted with sialyl and/or fucosyl residue, are provided for hydrogenolysis.

It is preferable that
the N-acetyl-lactosaminyl group in the glycosyl residue of $R_{2a}$ in general formula 1a is attached to the another N-acetyl-lactosaminyl group with 1-3 interglycosidic linkage,
the lacto-N-biosyl group in the glycosyl residue of $R_{2a}$ in general formula 1a is attached to the N-acetyl-lactosaminyl group with 1-3 interglycosidic linkage,
the lacto-N-biosyl group in the glycosyl residue of $R_{3a}$ in general formula 1a is attached to the N-acetyl-lactosaminyl group with 1-3 interglycosidic linkage,
the N-acetyl-lactosaminyl group in the glycosyl residue of $R_{3b}$ in general formula 1b is attached to the another N-acetyl-lactosaminyl group with 1-3 or 1-6 interglycosidic linkage,
the lacto-N-biosyl group in the glycosyl residue of $R_{3b}$ in general formula 1b is attached to the N-acetyl-lactosaminyl group with 1-3 interglycosidic linkage.

It is further preferable that compounds of general formula 1a and 1b, wherein general formula 1a represents the R-glycosides of lacto-N-neotetraose, para-lacto-N-hexaose, para-lacto-N-neohexaose, lacto-N-neohexaose, para-lacto-N-octaose and lacto-N-neooctaose optionally substituted with one or more sialyl and/or fucosyl residue, and general formula 1b represents the R-glycosides of lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue.

Particularly preferable compounds used for hydrogenolysis of general formula 1 and 2 are wherein:
the fucosyl residue attached to the N-acetyl-lactosaminyl and/or the lacto-N-biosyl group is linked to
the galactose of the lacto-N-biosyl group with 1-2 interglycosidic linkage and/or
the N-acetyl-glucosamine of the lacto-N-biosyl group with 1-4 interglycosidic linkage and/or
the N-acetyl-glucosamine of the N-acetyl-lactosaminyl group with 1-3 interglycosidic linkage,
the sialyl residue attached to the N-acetyl-lactosaminyl and/or the lacto-N-biosyl group is linked to
the galactose of the lacto-N-biosyl group with 2-3 interglycosidic linkage and/or
the N-acetyl-glucosamine of the lacto-N-biosyl group with 2-6 interglycosidic linkage and/or
the galactose of the N-acetyl-lactosaminyl group with 2-6 interglycosidic linkage.

The most preferable R-glycosides provided for hydrogenolysis represent naturally occurring HMOs having a lactose, LNT or LNnT core, and are selected from the group of: R-glycosides of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II.

According to another preferred embodiment, the compounds used in hydrogenolysis specified above are β-glycosides, more preferably the aglycon is benzyl.

The individual compounds comprised in the mixture or blend ready for hydrogenolysis can be synthesized by chemical, enzymatic or chemo-enzymatic way. For example the production of 1-O-benzyl/substituted benzyl-LNnT is described in Ponpipom et al. *Tetrahedron Lett.* 20, 1717 (1978) and in international application PCT/DK2011/050053; 1-O-benzyl/substituted benzyl-6'-SL and their salt are disclosed in international application PCT/DK2011/050052; the production of 1-O-benzyl-LNT is published in Liu et al. *Bioorg. Med. Chem.* 17, 4910 (2009); 1-O-benzyl-3'-SL sodium salt is specified in international application WO 96/32492 A1.

Mixture or blend of compounds of general formulae 1 and 2 can be produced in the following way. A method is performed, which method comprises the step of
a) providing at least one fucosyl, sialyl, N-acetyllactosaminyl or lacto-N-biosyl donor,
b) providing at least one acceptor selected from lactose R-glycoside, LNT R-glycoside and LNT R-glycoside, wherein R means as defined above,
c) preparing a blend from compounds provided by steps a) and b);

d) adding at least one enzyme comprising a transglycosidase activity and/or a glycosynthase activity to the blend of step c) thereby forming a mixture;

e) incubating the mixture obtained according to step d); and f) optionally repeating any of steps a) to d), preferably with the mixture obtained according to step e).

According to step a) at least one fucosyl, sialyl, N-acetyllactosaminyl or lacto-N-biosyl donor is provided and according to step b) at least one acceptor is provided. In the context of the present invention, the term "fucosyl, sialyl, N-acetyllactosaminyl or lacto-N-biosyl donor" is preferably understood as compounds, which provide or transfer a fucosyl, sialyl, N-acetyllactosaminyl or lacto-N-biosyl moiety in a chemical reaction, e.g. an enzymatic glycosylation, to a further compound, preferably an acceptor. Such "fucosyl, sialyl, N-acetyllactosaminyl or lacto-N-biosyl donors" are advanced or activated glycosyl compounds like e.g. glycosyl fluorides, glycosyl azides, optionally substituted phenyl glycosides, optionally substituted pyridinyl glycosides, optionally substituted 3-oxo-(2H)-furan-4-yl glycosides, optionally substituted 1,3,5-triazinyl glycosides or 4-methylumbelliferyl glycosides.

According to step c) a blend prepared from compounds provided by steps a) and b). Preferably, such a blend according to step c) represents a blend of one, two, three, four, five, one to five, three to ten, five to ten or even more preferably different compounds as defined according to step a) and one, two, three, four, five, one to five, three to ten, five to ten or even more preferably different compounds as defined according to step b).

In step d) of the inventive method for generating human milk oligosaccharides (HMOs) at least one enzyme comprising a transglycosidase activity and/or a glycosynthase activity is added to the blend obtained according to step c) of the inventive method, thereby forming a mixture.

In step d) at least one enzyme comprising transglycosidase activity and/or glycosynthase activity is added, preferably at least two (preferably different), three (preferably different), four (preferably different), five (preferably different), two to five (preferably different), two to ten (preferably different), two to twenty (preferably different), five to ten (preferably different) or even more preferably different enzymes comprising transglycosidase activity and/or glycosynthase activity.

Enzymes suitable in step d) typically comprise at least one enzyme comprising a transglycosidase activity and/or a glycosynthase activity, preferably selected from enzymes having, e.g. transglycosidase activity and/or a glycosynthase activity, e.g. having a fucosidase or trans-fucosidase, a sialidase (neuraminidase) or trans-sialidase (transneuraminidase), a lacto-N-biosidase or trans-lacto-N-biosidase and/or a N-acetyllactoaminidase or trans-N-acetyllactoaminidase activity, or any further enzyme having such an activity. Even more preferably, enzymes suitable in step d) may be selected from the group comprising wild type or mutated glycosidases or transglycosidases, preferably wild type or mutated glycosidases or transglycosidases having a fucosidase or trans-fucosidase, a sialidase (neuraminidase) or trans-sialidase (transneuraminidase), a lacto-N-biosidase or trans-lacto-N-biosidase and/or a N-acetyllactoaminidase or trans-N-acetyllactoaminidase activity, or preferably having α-trans-fucosidase, α-trans-sialidase, β-trans-Lacto-N-biosidase and/or β-trans-N-acetyllactosaminidase activity.

Enzymes suitable in step d) furthermore may be selected from any genus known to a skilled person, to express or secrete at least one enzyme as defined above, e.g. an enzyme having a transglycosidase activity and/or a glycosynthase activity, preferably an enzyme having a fucosidase or trans-fucosidase, a sialidase (neuraminidase) or trans-sialidase (transneuraminidase), a lacto-N-biosidase or trans-lacto-N-biosidase and/or a N-acetyllactoaminidase or trans-N-acetyllactoaminidase activity, or preferably having α-trans-fucosidase, α-trans-sialidase, β-trans-Lacto-N-biosidase and/or β-trans-N-acetyllactosaminidase activity, or any further enzyme having such an activity. Even more preferably, such enzymes suitable in step d) may be selected from bacteria selected from *Bacillus*, *Bifidobacterium*, *Lactobacillus*, *Leuconostoc*, *Lactococcus*, *Streptococcus*, *Streptomyces*, *Sulfolobus*, *Thermotoga*, or *Trypanosoma*.

The mixture is incubated in a further step e). Such an incubation advantageously allows to generate a multiplicity of different compound characterized by general formulae 1 and 2 defined above. Generation of such a multiplicity of different compounds is based on the use of enzymes with different activities during step d) but also on the use of diverse donors and acceptors according to steps a) and b), preferably as a blend as already outlined in step c). Utilizing this approach, the method advantageously allows to vary the possible number and type of oligosaccharides obtainable by the synthesis in a simple and cost efficient manner. The use of enzymes furthermore allows carrying out the preparation of various derivatives in a stereoselective manner. Generation of compounds preferably occurs by transferring N-acetyllactosaminyl moieties, lacto-N-biosyl moieties, fucosyl moieties, silyl moieties, by forming new bonds at desired positions of the molecule, etc., in a well defined manner to obtain a mixture of various human milk oligosaccharides R-glycosides.

Incubation according to step e) occurs with a concentration of (each of the) enzymes in a concentration of 1 mU/l to 1,000 U/l, preferably 10 mU/l to 100 U/l, when the activity capable of forming 1 mu mol of specific product for a defined protein starting from a defined educt is defined as 1 unit (U), e.g. for a glycotransferase the production of a glycose-containing complex carbohydrate at 37° C. in 1 minute. The activity of each enzyme as defined herein may be assessed with respect to its naturally occurring or engineered substrate.

The incubation according to step e) may be carried out in a reaction medium, preferably an aqueous medium, comprising the mixture obtained according to step d) and optionally water; a buffer such as a phosphate buffer, a carbonate buffer, an acetate buffer, a borate buffer, a citrate buffer and a tris buffer, or combinations thereof; alcohol, such as methanol and ethanol; ester such as ethyl acetate; ketone such as acetone; amide such as acetamide; and the like.

Furthermore, the incubation according to step e) may be carried out in a reaction medium as defined above, wherein optionally a surfactant or an organic solvent may be added, if necessary. Any surfactant capable of accelerating the formation of a complex carbohydrate as defined according to the present invention as a possible product of the invention can be used as the surfactant. Examples include nonionic surfactants such as polyoxyethylene octadecylamine (e.g., Nymeen S-215, manufactured by Nippon Oil & Fats); cationic surfactants, such as cetyltrimethylammonium bromide and alkyldimethyl benzylammoniumchloride (e.g., Cation F2-40E, manufactured by Nippon Oil & Fats); anionic surfactants such as lauroyl sarcosinate; tertiary amines such as alkyldimethylamine (e.g., Tertiary Amine FB, manufactured by Nippon Oil & Fats); and the like, which are used alone or as a mixture of two or more. The surfactant may be used generally in a concentration of 0.1 to 50 g/l. The organic solvent may include xylene, toluene, fatty acid alcohol, acetone, ethyl acetate, and the like, which may be used in a concentration of generally 0.1 to 50 ml/l.

The incubation according to step e) may be furthermore carried out in a reaction medium as defined above, preferably having a pH 3 to 10, pH 5 to 10, preferably pH 6 to 8.

The incubation according to step e) may be furthermore carried out at a temperature of about 0° C. to about 100° C., preferably at a temperature of about 10 to about 50° C., e.g. at a temperature of about 20° C. to about 50° C. In the reaction medium, inorganic salts, such as $MnCl_2$ and $MgCl_2$, may be added, if necessary.

The incubation according to step e) may be carried out in a bioreactor. The bioreactor is preferably suitable for either a continuous mode or a discontinuous mode.

The method of catalytic hydrogenolysis of compounds of general formulae 1 and 2 provides a mixture of human milk oligosaccharides (HMOs), the single compounds of which may be defined according to general formulae 3 and 4 respectively.

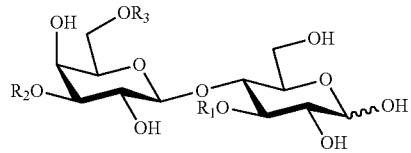

general formula 3

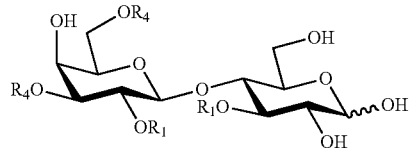

general formula 4

$R_1$ is independently fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue,
$R_4$ is independently sialyl or H,
and salts thereof,
with the proviso that at least one of $R_1$ or $R_4$ is not H in general formula 4.

HMO components produced by hydrogenolysis as defined above, particularly components as defined under general formulae 3a, 3b and 4

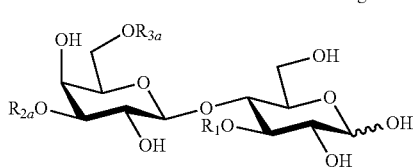

general formula 3a

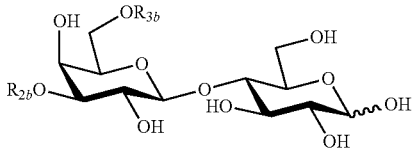

general formula 3b

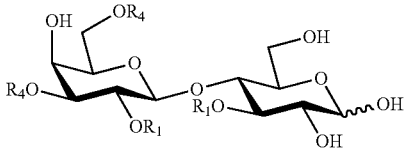

general formula 4 wherein $R_1$ and $R_4$ are as defined above,
$R_{2a}$ is N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue,
$R_{3a}$ is H or N-acetyl-lactosaminyl group optionally substituted with a lacto-N-biosyl group; any N-acetyl-lactosaminyl and lacto-N-biosyl group can be substituted with one or more sialyl and/or fucosyl residue,
$R_{2b}$ is lacto-N-biosyl group optionally substituted with sialyl and/or fucosyl residue.

More preferably, compounds are obtained after hydrogenolysis, wherein
the N-acetyl-lactosaminyl group in the glycosyl residue of $R_{2a}$ in general formula 3a is attached to the another N-acetyl-lactosaminyl group with 1-3 interglycosidic linkage,
the lacto-N-biosyl group in the glycosyl residue of $R_{2a}$ in general formula 3a is attached to the N-acetyl-lactosaminyl group with 1-3 interglycosidic linkage,
the lacto-N-biosyl group in the glycosyl residue of $R_{3a}$ in general formula 3a is attached to the N-acetyl-lactosaminyl group with 1-3 interglycosidic linkage,
the N-acetyl-lactosaminyl group in the glycosyl residue of $R_{3b}$ in general formula 3b is attached to the another N-acetyl-lactosaminyl group with 1-3 or 1-6 interglycosidic linkage,
the lacto-N-biosyl group in the glycosyl residue of $R_{3b}$ in general formula 3b is attached to the N-acetyl-lactosaminyl group with 1-3 interglycosidic linkage.

Even more preferable compounds obtained after hydrogenolysis are compounds of general formula 3a and 3b, wherein general formula 3a represents lacto-N-neotetraose, para-lacto-N-hexaose, para-lacto-N-neohexaose, lacto-N-neohexaose, para-lacto-N-octaose and lacto-N-neooctaose optionally substituted with one or more sialyl and/or fucosyl residue, and general formula 3b represents lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue.

Particularly preferable compounds as products of hydrogenolysis are wherein
the fucosyl residue attached to the N-acetyl-lactosaminyl and/or the lacto-N-biosyl group is linked to
the galactose of the lacto-N-biosyl group with 1-2 interglycosidic linkage and/or
the N-acetyl-glucosamine of the lacto-N-biosyl group with 1-4 interglycosidic linkage and/or the N-acetyl-glucosamine of the N-acetyl-lactosaminyl group with 1-3 interglycosidic linkage, the sialyl residue attached to the N-acetyl-lactosaminyl and/or the lacto-N-biosyl group is linked to the galactose of the lacto-N-biosyl group with 2-3 interglycosidic linkage and/or the N-acetyl-glucosamine of the lacto-N-biosyl group with 2-6 interglycosidic linkage and/or the galactose of the N-acetyl-lactosaminyl group with 2-6 interglycosidic linkage.

The most preferable compounds obtained in hydrogenolysis represent naturally occurring HMOs having a lactose, LNT or LNnT core, and are selected from the group of: 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II.

An advantage of the present invention is that it can be used to provide a mixture of HMOs whose composition is substantially similar to that of the natural human milk. In other words a quantity of the starting mixture comprising compounds of general formulae 1, 1a, 1b and 2 can be selected such that when they undergo catalytic hydrogenolysis the final product mixture of HMOs according to general formulae 3 and 4 has a HMO profile which is substantially similar to those found in natural human milk. Furthermore as the catalytic hydrogenolysis proceeds practically without by-product formation and almost quantitatively, the composition of the starting mixture comprising compounds of general formulae general formulae 1, 1a, 1b and 2 is directly proportional to the final product mixture of HMOs. Thus careful tuning of the starting materials leads compositions analogue to human milk.

For the purpose of the present invention, a "substantially similar profile of oligosaccharides" is meant to be a profile of oligosaccharides in which the quantity of all of the considered oligosaccharides differs by less than 25%, preferably less than 15%, more preferably less than 5%, most preferably less than 1%, in comparison to the quantity if the corresponding oligosaccharides in the reference. For the purpose of the present invention the reference oligosaccharide quantity shall be derived from milk of mothers with a similar genetic background with respect to the enzymes responsible for the natural formation of said oligosaccharides in mammary glands.

For example, if the mixture considered comprises 2 oligosaccharides A and B and is evaluated in reference to human milk, the oligosaccharide profile of the mixture will be said "substantially similar" in reference to human milk if the amount of A and the amount of B each differs by less than 25% (preferably less than 15%, more preferably less than 5%, most preferably less than 1%) from the amount of A and B in the reference human milk.

When the reference is human milk, the reference is taken from values commonly found in literature representing the average composition of human milk based on a significant pool of samples analysis. Such values are reflected in Table 1.

In another embodiment of the invention such "substantially similar profile" is measured by comparing the ratios of the considered oligosaccharides in the subject nutritional composition. The ratios are selected to be similar to the ratios naturally occurring in human milk.

The content of certain oligosaccharides (in g/l) in human breast milk varies at different stages of lactation in females as shown in table 1.

TABLE 1 content of certain oligosaccharides (in g/l) in human breast milk at different stages of lactation.

| HMO (g/l) | Colostrum breast milk (<5 days lactation) | Transitional breast milk (5-10 days lactation) | Mature breast milk (>10 days lactation) |
|---|---|---|---|
| LNnT | 0.11-0.6 | 0.4-0.5 | 0.15-0.3 |
| LNT | 0-3 | 3.9 | 0.5-1.5 |
| 2FL | 0-5 | 0-2.7 | 0-2.5 |
| 6SL | 0.3-0.4 | 0.5-0.8 | 0.4 |
| 3SL | 0.2-0.4 | 0.1-0.3 | 0.5 |
| Sialic acid | 0.06 | 0.034 | 0.031 |
| Total | >10 | 10 | 5-8 |

Table 2 below shows an exemplary embodiment of the invention in which the proportions of HMOs in human milk are shown and the proportions of oligosaccharides to be provided in an infant formula.

TABLE 2

Typical ratios of HMOs in human milk and infant nutritional product of the invention (such as infant formula)

| HMO (g/l) | Human milk range | Target Infant Formula | Ratio example relative to 2FL (considered HMO/2FL) |
|---|---|---|---|
| LNnT | 0.1-0.6 | 0.1-0.6 | 0.1 =< R =< 50 Preferably 0.5 =< R =< 20 |
| LNT | 0-4 | 0-4 | 0.5 =< R =< 50 Preferably 1 =< R =< 5 |
| 2FL | 0-5 | 0-5 | NA |
| 6SL | 0.3-0.8 | 0-0.8 | 0.1 =< R =< 30 Preferably 1 =< R =< 5 |
| 3SL | 0.2-0.4 | 0-0.4 | 0.05 < R < 30 Preferably 0.05 =< R =< 5 |
| Sialic acid (SA) | 0-0.06 | 0-0.06 | 0.005 < R < 0.1 Preferably 0.01 =< R =< 0.05 |
| Total OS | >10 | | |

Table 3 below shows an exemplary embodiment of the invention in which the proportions of HMOs in human milk are shown and the proportions of oligosaccharides to be provided in an infant formula.

TABLE 3

Typical ratios of HMOs in human milk and infant nutritional product of the invention (such as infant formula).

| HMO (g/l) | Human milk range | Target infant formula | Ratio example relative to LNT (LNT/considered HMO) |
|---|---|---|---|
| LNnT | 0.1-0.6 | 0.1-0.6 | 0.05 =< R =< 0.2 |
| LNT | 0-4 | 0-4 | na |
| 2FL | 0-5 | 0-5 | 0.5 =< R =< 5 |
| 6SL | 0.3-0.8 | 0-0.8 | 0.05 =< R =< 0.5 |
| 3SL | 0.2-0.4 | 0-0.4 | 0.5 =< R =< 5 |
| Sialic acid (SA) | 0-0.06 | 0-0.06 | 5 =< R =< 50 |
| Total OS | >10 | | |

TABLE 3-continued

Typical ratios of HMOs in human milk and infant nutritional product of the invention (such as infant formula).

| HMO (g/l) | Human milk range | Target infant formula | Ratio example relative to LNT (LNT/considered HMO) |
|---|---|---|---|

The invention encompasses the ratios that can be deducted and/or calculated from the ratios as shown in table 2 and 3.

It has been found that the ratios cited in the above tables or calculated from the above tables are particularly relevant in the context of infant nutritional products, in particular infant formula. When obtained by the process described herein and when the ratios of the HMOs precursors are selected to obtain the desired HMOs ratios in the product (as per table 2 and 3 or calculated from tables 2 or 3), the invention presents the particular advantage of making/providing a mixture of HMOs that is most directly suitable for the use in infant nutritional products such as infant formula.

The mixture of human milk oligosaccharides made by the present invention can be used in a consumable product, in particular pharmaceutical and nutritional use. The mixture of human milk oligosaccharides is particularly effective in the education and/or maturation of the immune system of neonatal infants, and has preventive effect against secondary infections following viral infections such as influenza.

The mixture of human milk oligosaccharides as a prebiotic enhances the beneficial effects and efficiency of probiotics, such as, but not limited to *Lactobacillus* and *Bifidobacterium* species, in promoting the development of an early bifidogenic intestinal microbiota in infants, in reducing the risk of development of allergy and/or asthma in infants, in preventing and treating pathogenic infections in such as diarrhoea in infants. Furthermore additional probiotics can be added, e.g. lacto bacteria, *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet can also be further added.

The mixture of human milk oligosaccharides can be added to a pharmaceutically acceptable carriers such as, but not limited to additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.). Suitable carriers are described in the most recent edition of Remington's Pharmaceutical Sciences, a standard reference text in the field. When the mixture of human milk oligosaccharides is added to the pharmaceutically acceptable carriers a dosage form in the form of for example, but not limited to tablets, powders, granules, suspensions, emulsions, infusions, capsules, injections, liquids, elixirs, extracts and tincture can be formed. In a further embodiment the consumable product can be nutritional formulation such as foods, drinks or feeds, containing edible micronutrients, vitamins and minerals. The amounts of such ingredient may vary depending on whether the consumable product is intended for use with healthy infants, children, adults or subjects having specialized needs (e.g. suffering from metabolic disorders). Micronutrients include for example edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolyzed cornstarch, etc.) and proteins from casein, soy-bean, whey or skim milk, or hydrolysates of these proteins, but protein from other source (either intact or hydrolysed) may be used as well. Vitamins may be chosen such as vitamin A, B1, B2, B5, B6, B12, C, D, E, H, K, folic acid, inositol and nicotinic acid. The nutritional formula may contain the following minerals and trace elements: Ca, P, K, Na, Cl, Mg, Mn, Fe, Cu, Zn, Se, Cr or I.

In a further embodiment the consumable product can be infant formula. In the context of the present invention, the term "infant formula" preferably means a foodstuff intended for particular nutritional use by infants during the first 4-6 months or even 4 to 12 months of life and satisfying by itself the nutritional requirements of infants. It may contain one or more probiotic *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet.

In a further embodiment the consumable product can be a food supplement. Such a food supplement preferably contains ingredients as defined for nutritional food above, e.g. vitamins, minerals, trace elements and other micronutritients, etc. The food supplement may be for example in the form of tablets, capsules, pastilles or a liquid. The supplement may contain conventional additives selected from but not limited to binders, coatings, emulsifiers, solubilising agents, encapsulating agents, film forming agents, adsorbents, carriers, fillers, dispersing agents, wetting agents, jellifying agents, gel forming agents, etc.

The consumable product can also be as mentioned an infant nutritional product, for example for an infant up to the age of 3. The consumable product can also be part of baby food, infant cereal, growing-up milks or the like. In one embodiment the consumable product or infant nutritional product is a weaning food.

In a further embodiment the consumable product can be digestive health functional food as the administration of compounds as prepared according to the present invention, more preferably a diversified blend of HMOs, as may be prepared by the inventive method, provides a beneficial effect on digestive health. Digestive health functional food is preferably a processed food used with intention to enhance and preserve digestive health by utilizing compounds as prepared according to the present invention, more preferably a diversified blend of HMOs, as may be prepared by the inventive method, as physiologically functional ingredients or components in forms of tablet, capsule, powder, etc. Different terms such as dietary supplement, nutraceutical, designed food, health product may also be used to refer to digestive health functional food.

In a further embodiment the consumable product or infant nutritional product of the invention further comprises probiotics. Probiotics are used to beneficially utilize, metabolize or grow preferentially on the HMOs of the invention. The probiotics can be selected from the probiotics known in the art of infant formula.

In one embodiment of the invention, the nutritional product or the infant formula is man-made or synthetically made. It can be made from a mixture of ingredients isolated from nature, from ingredients made by chemical processes, biological processes, microbiological processes, or mixtures thereof, In one embodiment of the invention the nutritional product or the infant formula is partly made with human breast milk or is intended to be mixed with human breast milk to supplement it and achieved a higher nutritional value (this is especially considered in case of deficiencies of the human breast milk as for specific nutrients).

Example 1

Mixtures of compounds by general formula 1 and 2 were dissolved in a protic solvent such as water or alcohol or mixtures thereof (4 volumes) and 10% Pd on charcoal (1/10 weight compared to the weight of starting carbohydrates) was added, and the pH of the solution was adjusted to 4-6 by addition of an acid such as, but not limited to HCl, sialic acid or citric acid to form a suspension. The suspension was treated with hydrogen gas (5-6 bar) at 54° C. whilst being stirred. The hydrogenolysis was complete within 2-3 hours. The resulting suspension was filtered to provide a solid product. The final product is washed with warm water and dried to provide the mixture of the HMOs

Example 2

A mixture of 1-O-benzyl-LNT (0.3 g), 1-O-benzyl-LNnT (0.3 g)), 1-O-benzyl-2'-FL (0.3 g) and 1-O-benzyl-6'-SL (0.3 g) was dissolved in 4.8 ml of water to form a solution. To the solution 0.12 g of 10% Pd/C was added, followed by the addition of concentrated HCl until the pH of the solution is pH 4. The suspension was treated with hydrogen gas (5-6 bar) at 54° C. whilst being stirred. The resulting suspension was filtered to provide a solid product of a mixture of HMOs of LNT/LNnT/2'-FL/6'-SL.

Example 3

Infant Formulation

An example of the composition of an infant formula according to the present invention is given in table 4 below. This composition is given by way of illustration only. Another example is based on commercial NAN HA Infant formula (hypoallergenic with hydrolyzed proteins) or non HA conventional infant formula (from Nestlé, Switzerland) to which the specific oligosaccharides of the invention are added as in the amount stated below.

TABLE 4

Composition of an infant formula according to an aspect of the present invention

| Nutrient | per 100 kcal | per litre |
|---|---|---|
| Energy (kcal) | 100 | 670 |
| Protein Hydrolysate (g) 77% NTN/TN 10% TBNS reactive lysineN/TN | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Optional Prebiotic (90% GOS, 10% inulin or FOS) (g) | 0.64 | 4.3 |
| Minerals (g) | 0.37 | 2.5 |

TABLE 4-continued

Composition of an infant formula according to an aspect of the present invention

| Nutrient | per 100 kcal | per litre |
|---|---|---|
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| 3'sialyllactose (mg) | 30 | 200 |
| 6'sialyllactose (mg) | 6 | 40 |
| LNnT (mg) | 30 | 200 |
| 2FL (mg) | 300 | 2000 |

Further examples of infant formula according to the present invention are proposed, in which the HMOs according to the tables below replace the HMOs shown in table 4:

| | | |
|---|---|---|
| 3'sialyllactose (mg) | 15 | 100 |
| 6'sialyllactose (mg) | 3 | 20 |
| LNnT (mg) | 45 | 300 |
| 2FL (mg) | 150 | 1000 | or

| | | |
|---|---|---|
| LNnT (mg) | 45 | 300 |
| 6'sialyllactose (mg) | 105 | 700 |
| LNT (mg) | 300 | 2000 |
| Optionally 2FL (mg) | Optionally 150 | Optionally 1000 |

Or

| | | |
|---|---|---|
| LNnT (mg) | 45 | 300 |
| 3'sialyllactose (mg) | 15 | 100 |
| 6'sialyllactose (mg) | 105 | 700 |
| LNT (mg) | 150 | 1000 |
| 2FL (mg) | 150 | 1000 |

Or

| | | |
|---|---|---|
| LNnT (mg) | 45 | 300 |
| 3'sialyllactose (mg) | 15 | 100 |
| 6'sialyllactose (mg) | 3 | 20 |
| LNT (mg) | 150 | 1000 |
| 2FL (mg) | 150 | 1000 |

Or

| | | |
|---|---|---|
| LNnT (mg) | 45 | 300 |
| 3'sialyllactose (mg) | 15 | 100 |
| 6'sialyllactose (mg) | 75 | 500 |
| 2FL (mg) | 150 | 1000 |

Or

| | | |
|---|---|---|
| LNnT (mg) | 45 | 300 |
| LNT (mg) | 150 | 1000 |
| 6'sialyllactose (mg) | 75 | 500 |
| 2FL (mg) | 150 | 1000 |

Or

| | | |
|---|---|---|
| LNnT (mg) | 30 | 200 |
| 2FL (mg) | 150 | 1000 |

Example 4

A method of manufacturing an infant formula according to the invention will now be described by way of example only.

The mixture of HMOs is obtained by the method as described in the present document. An example of this mixture can contains approximately 1.5 grams per litre of a mixture of about 30 wt % GalNAcα1,3Galβ1,4Glc and Galβ1,6GalNAcα1,3Galβ1,4Glc, 50 wt % of Galβ1,6Galβ1,6Glc, Galβ1,6Galβ1,4Glc and Galβ1,3Galβ1,4Glc and 20 wt % of NeuAcα2,3Galβ1,4Glc and NeuAcα2,6Galβ1,4Glc. The mixture may either be added directly to a food product such as an infant formula or may by further concentrated in a manner known to those skilled in the art.

Example 5

An example of an infant formula containing an oligosaccharide according to the present invention is given below. It is based on commercial NAN and/or Lactogen Infant formulae (from Nestlé, Switzerland) to which the specific oligosaccharides of the invention are added as in the amount shown below.

| Nutrient | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Oligosaccharide mixture from Example 3 or 4 (g) | 0.15 | 1.0 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |

In further examples of the invention the HMOs are present in the infant nutritional product or infant formula (of example 5) in the quantities and/or ratios provided in the table 1, 2 or 3.

Example 6

Example 6 provides further examples of an infant formula of the invention. Alternatively the composition of the below table can be combined with the HMOs amounts provided under example 3 (with the alternatives) to form multiple embodiments of the invention.

| Nutrient | per 100 kcal | per litre |
|---|---|---|
| Energy (kcal) | 100 | 670 |
| Protein (g) | 1.89 | 12.6 |
| Fat (g) | 5.3 | 35.7 |
| Linoleic acid (g) | 0.82 | 5.5 |
| α-Linolenic acid (mg) | 101 | 675 |
| Lactose (g) | 10.8 | 72.4 |
| Lacto-N-neotetraose (LNNT)(g) | 0.083 | 0.56 |
| 2'Fucosyllactose (2FL)(g) | 0.17 | 1.14 |
| Minerals (g) | 0.405 | 2.7 |
| Na (mg) | 31 | 207 |
| K (mg) | 110 | 737 |
| Cl (mg) | 67 | 448 |
| Ca (mg) | 62 | 410 |
| P (mg) | 34 | 227 |
| Mg (mg) | 8.3 | 55 |
| Mn (μg) | 23 | 154 |
| Se (μg) | 2.5 | 16.8 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 0.92 | 6.2 |
| I (μg) | 20 | 132 |
| Cu (mg) | 0.07 | 0.47 |
| Zn (mg) | 0.96 | 6.5 |

In one embodiment of the invention the invention is adapted to pets. The pets oligosaccharides and the oligosaccharides profiles or ratios are adapted to correspond to the corresponding pet's milk. Such pets include cats, dogs, and horses.

Having thus described the present invention in detail and the advantages thereof, it is to be understood that the detailed description is not intended to limit the scope of the invention thereof. What is desired to be protected by letters patent is set forth in the following claims.

The invention claimed is:

1. A method for manufacturing an infant nutritional product or infant formula comprising a mixture of human milk oligosaccharides (HMOs), the method comprising: subjecting a mixture of at least two compounds selected from the group consisting of compounds of general formula 1 and compounds of general formula 2 to catalytic hydrogenolysis to remove,

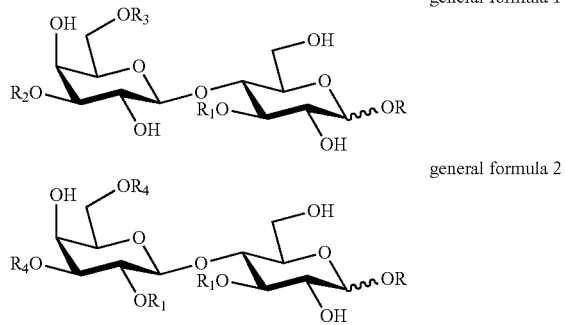

wherein R is a group removable by the catalytic hydrogenolysis,
$R_1$ is independently a fucosyl or an H,
$R_2$ is an N-acetyl-lactosaminyl group or a lacto-N-biosyl group,
$R_3$ is an H or an N-acetyl-lactosaminyl group
$R_4$ is independently a sialyl or an H,
and salts thereof,
at least one of $R_1$ or $R_4$ is not H in general formula 2, and
a quantity of the mixture of the at least two compounds selected from the group consisting of compounds of general formula 1 and compounds of general formula 2 are selected such that the mixture of human milk oligosaccharides (HMOs) has an oligosaccharide profile that is substantially similar to a milk selected from the group consisting of colostrum breast milk, transitional breast milk and mature breast milk.

2. The method of claim 1, wherein the catalytic hydrogenolysis is carried out in at least one protic solvent in the presence of a hydrogenolysis catalyst.

3. The method of claim 1, wherein the at least two compounds are selected from the group consisting of R-glycosides of 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II.

4. The method of claim 1, wherein the infant nutritional product or infant formula is in a form selected from the group consisting of a liquid, a powder or a solid.

5. The method of claim 1, comprising adding a component selected from the group consisting of pharmaceutically or nutritionally acceptable carriers, lactose, proteins, and fat to the mixture of human milk oligosaccharides.

6. The method of claim 1, further comprising adding prebiotics to the mixture of human milk oligosaccharides.

7. The method of claim 1, wherein the N-acetyl lactosaminyl group comprises a glycosyl residue comprising one or more N-acetyl-lactosaminyl and/or one or more lacto-N-biosyl groups, and at least one N-acetyl-lactosaminyl or lacto-N-biosyl group can be substituted with a sialyl and/or fucosyl residue; and $R_3$ is N-acetyl-lactosaminyl group substituted with a glycosyl residue comprising one or more N-acetyl-lactosaminyl and/or one or more lacto-N-biosyl groups, and at least one N-acetyl-lactosaminyl or lacto-N-biosyl group is substituted with a sialyl and/or fucosyl residue.

8. A method for manufacturing an infant nutritional product or infant formula comprising a mixture of human milk oligosaccharides (HMOs), the method comprising: subjecting a mixture of at least two compounds selected from the group consisting of compounds of general formula 1 and general formula 2 to catalytic hydrogenolysis to remove R,

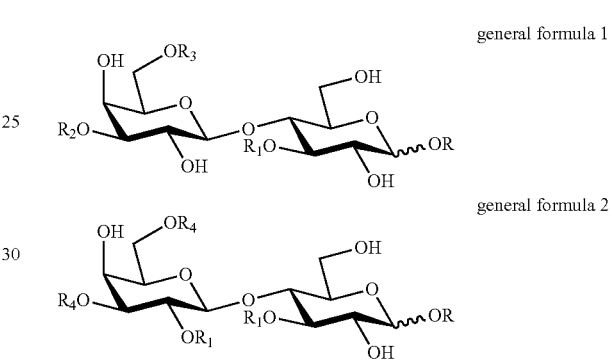

wherein R is a group removable by the catalytic hydrogenolysis,
$R_1$ is independently a fucosyl or an H,
$R_2$ is an N-acetyl-lactosaminyl group or a lacto-N-biosyl group,
$R_3$ is an H or an N-acetyl-lactosaminyl group,
$R_4$ is independently a sialyl or an H,
and salts thereof,
at least one of $R_1$ or $R_4$ is not H in general formula 2,
wherein the compounds of general formula 1 are selected from the group consisting of compounds of general formula 1a and compounds of general formula 1b,

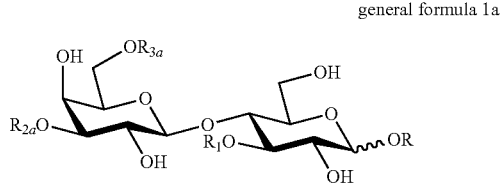

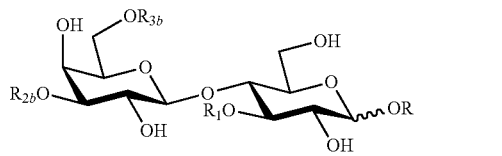

$R_{2a}$ is an N-acetyl-lactosaminyl group substituted with a glycosyl residue comprising one N-acetyl-lactosaminyl and/or one lacto-N-biosyl group; at least one N-acetyl-lactosaminyl or lacto-N-biosyl group is substituted with a sialyl and/or fucosyl residue, $R_{3a}$ is an H or an N-acetyl-lactosaminyl group substituted with a lacto-N-biosyl group; at least one N-acetyl-lactosaminyl or lacto-N-biosyl group is substituted with a sialyl and/or fucosyl residue, $R_{2b}$ is a lacto-N-biosyl group substituted with sialyl and/or fucosyl residue, and $R_{3b}$ is an H or an N-acetyl-lactosaminyl group substituted with one or two N-acetyl-lactosaminyl and/or one lacto-N-biosyl group; at least one N-acetyl-lactosaminyl or lacto-N-biosyl group is substituted with sialyl and/or fucosyl residue, and a quantity of the mixture of the at least two compounds selected from the group consisting of compounds of general formula 1 and compounds of general formula 2 are selected such that the mixture of human milk oligosaccharides (HMOs) has an oligosaccharide profile that is substantially similar to a milk selected from the group consisting of colostrum breast milk, transitional breast milk and mature breast milk.

9. The method of claim 8, wherein the N-acetyl-lactosaminyl group in the glycosyl residue of $R_{2a}$ in general formula 1a is attached to the another N-acetyl-lactosaminyl group with 1-3 interglycosidic linkage, the lacto-N-biosyl group in the glycosyl residue of $R_{2a}$ in general formula 1a is attached to the N-acetyl-lactosaminyl group with 1-3 interglycosidic linkage, the lacto-N-biosyl group in the glycosyl residue of $R_{3a}$ in general formula 1a is attached to the N-acetyl-lactosaminyl group with 1-3 interglycosidic linkage, the N-acetyl-lactosaminyl group in the glycosyl residue of $R_{3b}$ in general formula 1b is attached to the another N-acetyl-lactosaminyl group with 1-3 or 1-6 interglycosidic linkage, and/or the lacto-N-biosyl group in the glycosyl residue of $R_{3b}$ in general formula 1b is attached to the N-acetyl-lactosaminyl group with 1-3 interglycosidic linkage.

10. The method of claim 8, wherein general formula 1a represents the R-glycosides of lacto-N-neotetraose, para-lacto-N-hexaose, para-lacto-N-neohexaose, lacto-N-neohexaose, para-lacto-N-octaose and lacto-N-neooctaose substituted with one or more sialyl and/or fucosyl residue, and general formula 1b represents the R-glycosides of lacto-N-tetraose, lacto-N-hexaose, lacto-N-octaose, iso-lacto-N-octaose, lacto-N-decaose and lacto-N-neodecaose substituted with one or more sialyl and/or fucosyl residue.

11. A method for manufacturing an infant nutritional product or infant formula comprising a mixture of human milk oligosaccharides (HMOs), the method comprising: subjecting a mixture of at least two compounds selected from the group consisting of compounds of general formula 1 and general formula 2 to catalytic hydrogenolysis to remove R,

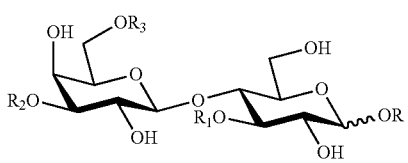

general formula 1

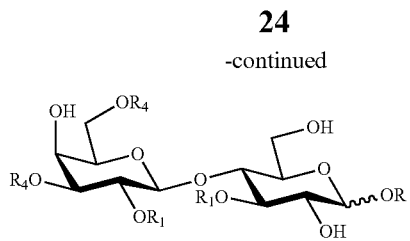

general formula 2 wherein R is a group removable by the catalytic hydrogenolysis, $R_1$ is independently a fucosyl or an H, $R_2$ is an N-acetyl-lactosaminyl group or a lacto-N-biosyl group, $R_3$ is an H or an N-acetyl-lactosaminyl group, $R_4$ is independently a sialyl or an H, and salts thereof, at least one of $R_1$ or $R_4$ is not H in general formula 2, the fucosyl residue attached to the N-acetyl-lactosaminyl and/or the lacto-N-biosyl group includes a linkage selected from the group consisting of the galactose of the lacto-N-biosyl group with 1-2 interglycosidic linkage, the N-acetyl-glucosamine of the lacto-N-biosyl group with 1-4 interglycosidic linkage, and the N-acetyl-glucosamine of the N-acetyl-lactosaminyl group with 1-3 interglycosidic linkage; and the sialyl residue attached to the N-acetyl-lactosaminyl and/or the lacto-N-biosyl group includes a linkage selected from the group consisting of the galactose of the lacto-N-biosyl group with 2-3 interglycosidic linkage, the N-acetyl-glucosamine of the lacto-N-biosyl group with 2-6 interglycosidic linkage, and the galactose of the N-acetyl-lactosaminyl group with 2-6 interglycosidic linkage, and a quantity of the mixture of the at least two compounds selected from the group consisting of compounds of general formula 1 and compounds of general formula 2 are selected such that the mixture of human milk oligosaccharides (HMOs) has an oligosaccharide profile that is substantially similar to a milk selected from the group consisting of colostrum breast milk, transitional breast milk and mature breast milk.

12. A method for manufacturing an infant nutritional product or infant formula comprising a mixture of human milk oligosaccharides (HMOs), the method comprising: subjecting a mixture of at least two compounds selected from the group consisting of compounds of general formula 1 and compounds of general formula 2 to catalytic hydrogenolysis to remove R,

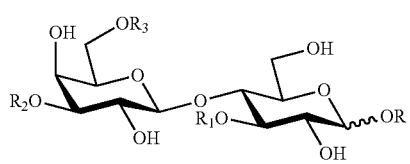

general formula 1

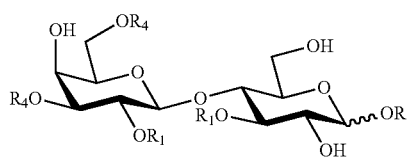

general formula 2 wherein the R-glycoside is a β-anomer,
$R_1$ is independently a fucosyl or an H,
$R_2$ is an N-acetyl-lactosaminyl group or a lacto-N-biosyl group,
$R_3$ is an H or an N-acetyl-lactosaminyl group,
$R_4$ is independently a sialyl or an H,
and salts thereof,
at least one of $R_1$ or $R_4$ is not H in general formula 2, and
a quantity of the mixture of the at least two compounds selected from the group consisting of compounds of general formula 1 and compounds of general formula 2 are selected such that the mixture of human milk oligosaccharides (HMOs) has an oligosaccharide profile that is substantially similar to a milk selected from the group consisting of colostrum breast milk, transitional breast milk and mature breast milk.

13. The method of claim 12, wherein the N-acetyl lactosaminyl group comprises a glycosyl residue comprising one or more N-acetyl-lactosaminyl and/or one or more lacto-N-biosyl groups, and at least one N-acetyl-lactosaminyl or lacto-N-biosyl group is substituted with a sialyl and/or fucosyl residue; and
   $R_3$ is N-acetyl-lactosaminyl group substituted with a glycosyl residue comprising one or more N-acetyl-lactosaminyl and/or one or more lacto-N-biosyl groups, and at least one N-acetyl-lactosaminyl or lacto-N-biosyl group is substituted with one or more sialyl and/or fucosyl residue.

14. A method for manufacturing an infant nutritional product or infant formula comprising a mixture of human milk oligosaccharides (HMOs), the method comprising: subjecting a mixture of at least two compounds selected from the group consisting of compounds of general formula 1 and compounds of general formula 2 to catalytic hydrogenolysis to remove R,

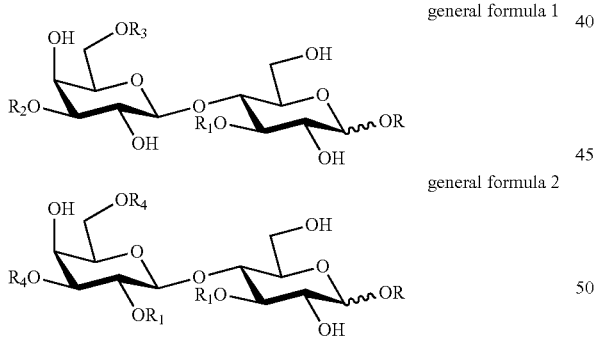

general formula 1 general formula 2 wherein R is a benzyl,
$R_1$ is independently a fucosyl or an H,
$R_2$ is an N-acetyl-lactosaminyl group or a lacto-N-biosyl group,
$R_3$ is an H or an N-acetyl-lactosaminyl group,
$R_4$ is independently a sialyl or an H,
and salts thereof,
at least one of $R_1$ or $R_4$ is not H in general formula 2, and
a quantity of the mixture of the at least two compounds selected from the group consisting of compounds of general formula 1 and compounds of general formula 2 are selected such that the mixture of human milk oligosaccharides (HMOs) has an oligosaccharide profile that is substantially similar to a milk selected from the group consisting of colostrum breast milk, transitional breast milk and mature breast milk.

15. The method of claim 14, wherein the N-acetyl lactosaminyl group comprises a glycosyl residue comprising one or more N-acetyl-lactosaminyl and/or one or more lacto-N-biosyl groups, and at least one N-acetyl-lactosaminyl or lacto-N-biosyl group can be substituted with a sialyl and/or fucosyl residue; and
   $R_3$ is N-acetyl-lactosaminyl group substituted with a glycosyl residue comprising one or more N-acetyl-lactosaminyl and/or one or more lacto-N-biosyl groups, and at least one N-acetyl-lactosaminyl or lacto-N-biosyl group can be substituted with one or more sialyl and/or fucosyl residue.

16. A method for manufacturing an infant nutritional product or infant formula comprising a mixture of human milk oligosaccharides (HMOs), the method comprising: subjecting a mixture of at least two compounds selected from the group consisting of compounds of general formula 1 and general formula 2 to catalytic hydrogenolysis to remove R,

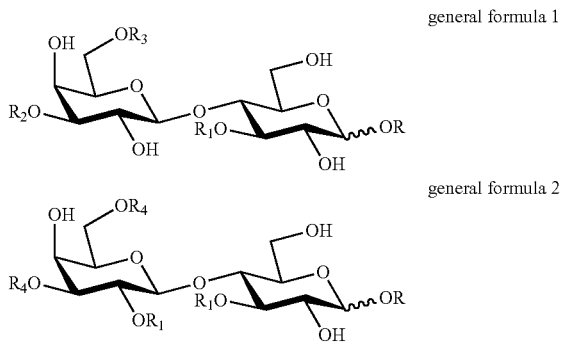

general formula 1 general formula 2 wherein R is a group removable by the catalytic hydrogenolysis,
$R_1$ is independently a fucosyl or an H,
$R_2$ is an N-acetyl-lactosaminyl group or a lacto-N-biosyl group,
$R_3$ is an H or an N-acetyl-lactosaminyl group,
$R_4$ is independently a sialyl or an H,
and salts thereof,
at least one of $R_1$ or $R_4$ is not H in general formula 2, and
a quantity of the mixture of the at least two compounds selected from the group consisting of compounds of general formula 1 and compounds of general formula 2 are selected such that the mixture of human milk oligosaccharides (HMOs) has an oligosaccharide profile that is substantially similar to a milk selected from the group consisting of colostrum breast milk, transitional breast milk and mature breast milk,
wherein the catalytic hydrogenation leads to human milk oligosaccharides (HMOs) according to general formula 3 and general formula 4

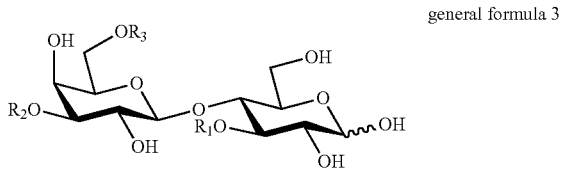

general formula 3 general formula 4

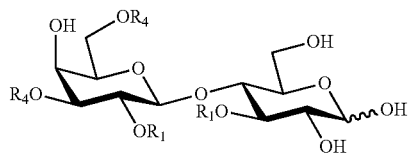

wherein $R_1$ is independently a fucosyl or an H,
$R_2$ is an N-acetyl-lactosaminyl group or a lacto-N-biosyl group,
$R_3$ is an H or an N-acetyl-lactosaminyl group,
$R_4$ is independently a sialyl or an H,
and salts thereof, and
at least one of $R_1$ or $R_4$ is not H in general formula 4.

17. The method of claim 16, wherein the HMOs are selected from the group consisting of: 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I and FDS-LNT II.

18. The method of claim 16, wherein the infant nutritional product or infant formula is in a form selected from the group consisting of a liquid, a powder and a solid.

19. The method of claim 16, comprising adding a component selected from the group consisting of pharmaceutically or nutritionally acceptable carriers, lactose, proteins, and fat to the mixture of human milk oligosaccharides.

20. The method of claim 16, further comprising adding prebiotics to the mixture of human milk oligosaccharides.

21. The method of claim 16, wherein the HMOs according to general formula 3 are characterized by general formula 3a and general formula 3b

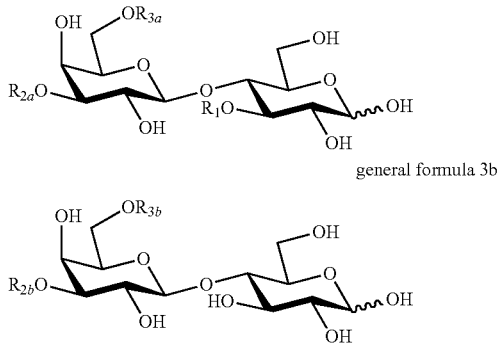

wherein
$R_{2a}$ is an N-acetyl-lactosaminyl group substituted with a glycosyl residue comprising one N-acetyl-lactosaminyl and/or one lacto-N-biosyl group; at least one N-acetyl-lactosaminyl or lacto-N-biosyl group is substituted with a sialyl and/or fucosyl residue, $R_{3a}$ is an H or an N-acetyl-lactosaminyl group substituted with a lacto-N-biosyl group; at least one N-acetyl-lactosaminyl or lacto-N-biosyl group is substituted with a sialyl and/or fucosyl residue, and $R_{2b}$ is lacto-N-biosyl group substituted with a sialyl and/or fucosyl residue.

22. The method of claim 21, wherein
the N-acetyl-lactosaminyl group in the glycosyl residue of $R_{2a}$ in general formula 3a is attached to the another N-acetyl-lactosaminyl group with 1-3 interglycosidic linkage,
the lacto-N-biosyl group in the glycosyl residue of $R_{2a}$ in general formula 3a is attached to the N-acetyl-lactosaminyl group with 1-3 interglycosidic linkage,
the lacto-N-biosyl group in the glycosyl residue of $R_{3a}$ in general formula 3a is attached to the N-acetyl-lactosaminyl group with 1-3 interglycosidic linkage,
the N-acetyl-lactosaminyl group in the glycosyl residue of $R_{3b}$ in general formula 3b is attached to the another N-acetyl-lactosaminyl group with 1-3 or 1-6 interglycosidic linkage, and and/or
the lacto-N-biosyl group in the glycosyl residue of $R_{3b}$ in general formula 3b is attached to the N-acetyl-lactosaminyl group with 1-3 interglycosidic linkage.

23. The method of claim 21, wherein general formula 3a represents lacto-N-neotetraose, para-lacto-N-hexaose, para-lacto-N-neohexaose, lacto-N-neohexaose, para-lacto-N-octaose and lacto-N-neooctaose optionally substituted with one or more sialyl and/or fucosyl residue, and general formula 3b represents lacto-N-tetraose, lacto-N-hexaose, lacto-N-octaose, iso-lacto-N-octaose, lacto-N-decaose and lacto-N-neodecaose optionally substituted with one or more sialyl and/or fucosyl residue.

24. The method of claim 21, wherein
the fucosyl residue attached to the N-acetyl-lactosaminyl and/or the lacto-N-biosyl group includes a linkage selected from the group consisting of
the galactose of the lacto-N-biosyl group with 1-2 interglycosidic linkage,
the N-acetyl-glucosamine of the lacto-N-biosyl group with 1-4 interglycosidic linkage and
the N-acetyl-glucosamine of the N-acetyl-lactosaminyl group with 1-3 interglycosidic linkage,
the sialyl residue attached to the N-acetyl-lactosaminyl and/or the lacto-N-biosyl group includes a linkage selected from the group consisting of
the galactose of the lacto-N-biosyl group with 2-3 interglycosidic linkage,
the N-acetyl-glucosamine of the lacto-N-biosyl group with 2-6 interglycosidic linkage, and
the galactose of the N-acetyl-lactosaminyl group with 2-6 interglycosidic linkage.

* * * * *